US009440947B2

(12) United States Patent
Lee et al.

(10) Patent No.: US 9,440,947 B2
(45) Date of Patent: Sep. 13, 2016

(54) REGENERATION OF SELECTIVE SOLVENTS FOR EXTRACTIVE PROCESSES

(71) Applicants: AMT International, Inc., Plano, TX (US); CPC Corporation, Taiwan, Taipei (TW)

(72) Inventors: Fu-Ming Lee, Katy, TX (US); Tzong-Bin Lin, Chia-Yi (TW); Kuang-Yeu Wu, Plano, TX (US); Jyh-Haur Hwang, Chia-Yi (TW); Jeffrey Tsung-Min Chiu, Taipei (TW); Jeng-Cheng Lee, Chia-Yi (TW); Yu-Ming Wu, Chia-Yi (TW); Han-Tjen Jan, Chia-Yi (TW)

(73) Assignees: AMT International, Inc., Plano, TX (US); CPC Corporation, Taiwan, Taipei (TW)

( * ) Notice: Subject to any disclaimer, the term of this patent is extended or adjusted under 35 U.S.C. 154(b) by 290 days.

(21) Appl. No.: 13/707,554

(22) Filed: Dec. 6, 2012

(65) Prior Publication Data

US 2013/0225838 A1    Aug. 29, 2013

Related U.S. Application Data

(60) Provisional application No. 61/603,338, filed on Feb. 26, 2012.

(51) Int. Cl.
*B01D 3/40* (2006.01)
*B01D 11/04* (2006.01)
(Continued)

(52) U.S. Cl.
CPC .............. *C07D 333/48* (2013.01); *B01D 3/40* (2013.01); *B01D 11/0484* (2013.01);
(Continued)

(58) Field of Classification Search
CPC .. B01D 3/40; B01D 11/0426; B01D 11/043; B01D 11/0434; B01D 11/0449; B01D 11/0457; B01D 11/0484; B01D 11/0488; B01D 11/0492; C07C 7/08; C07C 7/10; C07C 15/12; C10G 7/08; C10G 21/12; C10G 21/16; C10G 21/28; C10G 2300/44
USPC ........ 203/14, 42, 50, 53, 55, 57, 58, 64, 68, 203/70, 98, 99, 43–46; 208/311–313, 321, 208/325, 326, 330, 331, 333, 334, 41, 45, 208/314; 210/634, 638, 639, 695, 774, 805, 210/806; 549/87; 585/802, 804, 807, 810, 585/833, 857, 860, 864, 865, 867, 901
See application file for complete search history.

(56) References Cited

U.S. PATENT DOCUMENTS 3,344,202 A * 9/1967 Ziegenhain ................... 585/835
3,682,557 A * 8/1972 Simon et al. .................. 401/139
(Continued)

FOREIGN PATENT DOCUMENTS

| WO | 2009120181 A1 | 10/2009 |
| WO | 2012002132 A1 | 2/2012 |
| WO | 2012135111 A2 | 10/2012 |

OTHER PUBLICATIONS

PCT/US2012/069953 Search Report and Written Opinion Sep. 10, 2013.

*Primary Examiner* — Joseph Drodge
(74) *Attorney, Agent, or Firm* — Cascio & Zervas

(57) ABSTRACT

Recovering a polar hydrocarbon (HC) selective solvent substantially free of hydrocarbons (HCs) and other impurities from a lean solvent stream containing the selective solvent, measurable amounts of heavy aromatic HCs, and polymeric materials that are generated in an extractive distillation (ED) or liquid-liquid extraction (LLE) process. At least a portion of the lean solvent stream is contact in a solvent clean-up zone with a slip stream from the HC feed stream of the ED or LLE process or an external stream. The HC feed stream, such as pyrolysis gasoline or reformate, contains significant amounts of benzene and at least 50% polar (aromatic) HCs and serves as a displacement agent to remove the heavy HCs and polymeric material from the lean solvent stream. A magnetic filter can be used to remove the paramagnetic contaminants from the lean solvent.

30 Claims, 4 Drawing Sheets

(51) Int. Cl.
  *C07C 7/10*    (2006.01)
  *C07C 15/42*   (2006.01)
  *C10G 7/08*    (2006.01)
  *C10G 21/16*   (2006.01)
  *C10G 21/28*   (2006.01)
  *C07D 333/48*  (2006.01)
  *C07C 7/08*    (2006.01)
  *C10G 21/27*   (2006.01)

(52) U.S. Cl.
  CPC ............ *B01D 11/0488* (2013.01); *C07C 7/08* (2013.01); *C07C 7/10* (2013.01); *C10G 7/08* (2013.01); *C10G 21/16* (2013.01); *C10G 21/27* (2013.01); *C10G 21/28* (2013.01); *C10G 2300/44* (2013.01)

(56) References Cited

U.S. PATENT DOCUMENTS

| | | | |
|---|---|---|---|
| 3,775,259 A * | 11/1973 | Sarno | 203/54 |
| 4,018,657 A * | 4/1977 | Sweeney et al. | 203/38 |
| 4,046,676 A | 9/1977 | Asselin | |
| 4,048,062 A | 9/1977 | Asselin | |
| 4,820,849 A | 4/1989 | Diaz | |
| 5,053,137 A | 10/1991 | Lal | |
| 6,551,502 B1 * | 4/2003 | Lee et al. | 208/211 |
| 7,666,299 B2 | 2/2010 | Wu et al. | |
| 7,871,514 B2 | 1/2011 | Lee et al. | |
| 7,879,225 B2 * | 2/2011 | Lee et al. | 208/313 |
| 8,002,953 B2 * | 8/2011 | Lee et al. | 203/19 |
| 8,172,987 B2 * | 5/2012 | Lee et al. | 203/19 |
| 8,201,696 B2 * | 6/2012 | Monson | 210/511 |
| 8,246,811 B2 * | 8/2012 | Debuisschert et al. | 208/212 |
| 8,246,815 B2 | 8/2012 | Wu et al. | |
| 8,471,088 B2 * | 6/2013 | Monson et al. | 585/833 |
| 2007/0000809 A1 * | 1/2007 | Lin et al. | 208/254 R |
| 2009/0038991 A1 * | 2/2009 | Wu et al. | 208/49 |
| 2009/0105514 A1 * | 4/2009 | Lee et al. | 585/808 |
| 2009/0255853 A1 * | 10/2009 | Lee et al. | 208/312 |
| 2009/0272702 A1 | 11/2009 | Yen et al. | |
| 2010/0065504 A1 | 3/2010 | Yen et al. | |
| 2011/0094937 A1 * | 4/2011 | Subramanian et al. | 208/40 |
| 2011/0306816 A1 | 12/2011 | Cretoiu et al. | |
| 2012/0037542 A1 * | 2/2012 | Wu et al. | 208/313 |
| 2012/0165551 A1 | 6/2012 | Yen et al. | |
| 2012/0197057 A1 * | 8/2012 | Monson et al. | 585/857 |
| 2012/0228231 A1 | 9/2012 | Yen et al. | |

* cited by examiner

REGENERATION OF SELECTIVE SOLVENTS FOR EXTRACTIVE PROCESSES

CROSS-REFERENCE TO RELATED APPLICATIONS

This application claims priority to U.S. provisional patent application 61/603,338, filed Feb. 26, 2012, which is incorporated herein by reference.

BACKGROUND OF THE INVENTION

The most important commercial process for recovering benzene, toluene and xylene (BTX) aromatic hydrocarbons (HCs) from petroleum streams is liquid-liquid extraction (LLE) using sulfolane or polyalkylene glycol as the extractive solvent. Suitable petroleum streams include reformate, pyrolysis gasoline, coke oven oil, as well as coal tar. Extractive distillation (ED) using N-formyl morpholine as the extractive solvent is used extensively to recover benzene from coal tar and coke oven oil. ED using aqueous sulfolane solvent can recover benzene and toluene from reformate or pyrolysis gasoline after $C_8+$ fractions are removed from the feedstock.

The extractive solvents used in both ED and the LLE aromatics recovery processes are internally circulated indefinitely in a closed loop. Measurable amounts of hydrocarbon (HC) species, that are heavier than the intended feedstock, slip through even well-designed pretreatment units and accompany the feed stream into the extraction process. For a poorly operated or malfunctioned feed pretreatment unit, the level of heavy HCs in the feed stream can be significant. High concentrations of heavy HCs and polymeric materials that are generated by interactions among the heavy HCs, decomposed solvent, solvent additives and species from equipment corrosion lowers solvent performance and can even render the process inoperable.

SUMMARY OF THE INVENTION

The present invention is directed to an improved solvent regeneration system for the ED and LLE processes to remove the heavy HCs and polymeric materials that are otherwise trapped in the closed solvent loop by using non-aqueous displacement agents. This invention employs techniques for removing heavy HCs and polymeric sludge from a selective solvent. In one aspect, the invention is directed to a method of recovering a polar HC selective solvent substantially free of HCs and other impurities from a solvent-rich stream containing selective solvent, measurable amounts of heavy HCs, and polymeric materials generated from reactions among thermally decomposed or oxidized solvent, heavy HCs, and additives, which method includes the steps of:

(a) providing a feed stream containing polar and less polar HCs;

(b) introducing the feed stream into an extraction zone, which includes an extractive distillation column (EDC) or a liquid-liquid extraction (LLE) column, to yield (i) a less polar HC stream with an associated first water stream and (ii) a polar HC stream with associated lean solvent stream and second water stream; and (c) introducing a portion of the lean solvent stream into a solvent cleanup zone at a first location and introducing (i) a slip stream from the feed stream or (ii) an external stream comprising polar HCs and having a boiling point range that at least partially matches that of the feed stream into the solvent cleanup zone at a second location whereby (i) aromatic HCs in the slip stream or (ii) polar HCs in the external stream displace heavy HCs from the lean solvent stream thereby yielding a solvent phase that is introduced into the extraction zone and a HC phase that contains the displaced heavy HCs.

The HC feed stream, such as pyrolysis gasoline or reformate, contains significant amounts of benzene and usually at least 50% polar (aromatic) HCs, which have high affinity for the selective solvent. The invention is based in part on the recognition that the HC feed can serve as a displacement agent to remove the heavy HCs and polymeric material from the lean solvent. A filter that is enhanced with magnetic field can be installed in the lean solvent circulation line to work simultaneously with the solvent clean-up zone to remove the paramagnetic contaminants in the lean solvent. This magnetic filter minimizes and, in some cases, eliminates the need for a high temperature and energy intensive thermal solvent regenerator.

In one embodiment of the invention for aromatic HC recovery, a portion of the lean solvent in an ED or LLE process, which contains measurable amounts of heavy HCs and polymeric materials, is withdrawn from the bottom of a solvent recovery column and combined with regenerated solvent from an overhead of a thermal solvent regenerator. The combined stream is introduced into a low temperature, energy saving and easy-to-operate solvent clean-up zone after cooling. The solvent clean-up operation is typically conducted in a continuous multi-stage contacting device, and preferably in one that is designed for counter-current extraction. Suitable countercurrent designs include columns with entry and exit points at opposite ends usually at the upper and lower ends and incorporating trays, packings, or rotating discs and pulse columns. Non-concurrent designs include multi-stage mixers/settlers and rotating type contactors.

A slip stream from HC feed stream to the EDC in the ED process (or the LLE column in the LLE process) is introduced into the solvent clean-up zone, to contact the combined solvent stream. Preferably, the slip HC feed stream as the displacement agent contacts the combined solvent stream in a counter-current fashion in order to squeeze out the heavy HCs and polymeric materials from the solvent phase into the HC phase. The solvent phase, which contains essentially the solvent, most of the aromatic components in the HC feed slip stream (the displacement agent), especially benzene, and much reduced levels of heavy HCs and polymeric materials, is withdrawn continuously from the lower portion of the contactor and fed into the EDC (or the LLE column of a LLE process), as a part of the HC feed to this column as a way to recycle purified solvent into the closed solvent loop. A HC phase of the solvent clean up zone containing the "squeezed" heavy HCs and polymeric materials as well as most of non-aromatic components in the HC feed slip stream is accumulated on the top of the solvent clean-up contactor, removed continuously from the top of said contactor preferably under level control, and fed to a water wash column to remove any residual solvent in the HC phase. The solvent-clean-up zone is operated such that the benzene content of its HC phase after combining with the raffinate stream from the EDC (or LLE column), before or after the water wash column, is controlled at a desirable level. For example, if the combined HC stream is used for gasoline blending, its benzene concentration should be below one volume percent.

Alternatively, instead of employing a slip stream, any desulfurized light HC mixture, preferably containing polar (aromatic) HCs can be used as the displacement agent to remove the heavy HCs and polymeric materials from the lean solvent. With the present invention, the incorporation of a solvent clean-up zone to remove a substantial portion of the heavy HCs and polymeric materials greatly reduces the loading requirements of the conventional thermal solvent regenerator, when the latter is employed, and renders the process easier to operable, especially for the ED process.

Optionally, a magnetic filter can be installed in the solvent loop to selectively remove the paramagnetic contaminants generated from the interaction among decomposed solvent, various solvent additives and the heavy HCs with iron sulfides and iron oxides.

In another embodiment of the invention, a solvent regeneration scheme employs an efficient, low temperature and energy-saving solvent clean-up system. The process does not require the conventional high temperature and energy-intensive thermal solvent regenerator. A portion of a lean solvent stream that is withdrawn from the bottom of a solvent recovery column is diverted and introduced into a solvent clean-up zone after cooling. A slip stream from the HC feed stream to the EDC in the ED process (or the LLE column in the LLE process) is also fed to the solvent clean-up zone, to contact a diverted lean solvent stream.

The solvent clean-up operation can employ the same device as described above. The solvent phase containing essentially the solvent, most of aromatic components in the slip HC feed stream (the displacement agent), especially benzene, and much reduced levels of heavy HCs, is withdrawn continuously from the bottom of the contactor and fed to the ED or LLE column as a part of the HC feed. The HC phase containing the "squeezed" heavy HCs and polymeric materials is accumulated on the top of the contactor and is removed periodically or continuously from the contactor under interface level control. Alternatively, any desulfurized light HC mixture preferably containing polar (aromatic) HCs can be used as the displacement agent to remove heavy HCs and polymeric materials from the lean solvent. Again, a magnetic filter can be installed in the solvent loop to selectively remove the paramagnetic contaminants in the lean solvent stream.

For the above-described preferred embodiments, since the $C_9^+$ heavy HCs are recovered from the lean solvent in the solvent clean-up zone, the EDC in the ED process is preferably operated under such conditions as to maximize the benzene recovery by keeping substantially all $C_9^+$ HCs in the bottom of the EDC with the rich solvent (extract) stream. The solvent recovery column is preferably operated under such conditions as to strip only $C_8$ and lighter HCs from the rich solvent stream and to keep substantially all $C_9$ and heavier HCs in the bottom of the solvent recovery column with the lean solvent stream.

DETAILED DESCRIPTION OF PREFERRED EMBODIMENTS

The present invention can be integration into an ED or LLE process for the selective separation and recovery of polar HCs from a mixture containing the polar HCs and less polar HCs. The inventive processes are described in relation to the separation and recovery of aromatic HCs from mixtures containing aromatics and non-aromatics, including paraffins, isoparaffins, naphthenes, and/or olefins, but it is understood that the techniques are applicable to a multitude of HC mixtures. Suitable extractive solvents include, for example, sulfolane, alkyl-sulfolane, N-formyl morpholine, N-methylpyrrolidone, tetraethylene glycol, triethylene glycol, diethylene glycol, and mixtures thereof, with water as the co-solvent. For aromatic HC recovery, the preferred solvents for the ED process comprise sulfolane with water as the co-solvent and non-aqueous N-formyl morpholine; the preferred solvents for the LLE process comprise sulfolane and tetraethylene glycol and both with water as the co-solvent. The most preferred solvent for both the ED and LLE processes is sulfolane with water as the co-solvent.

Figure 1:
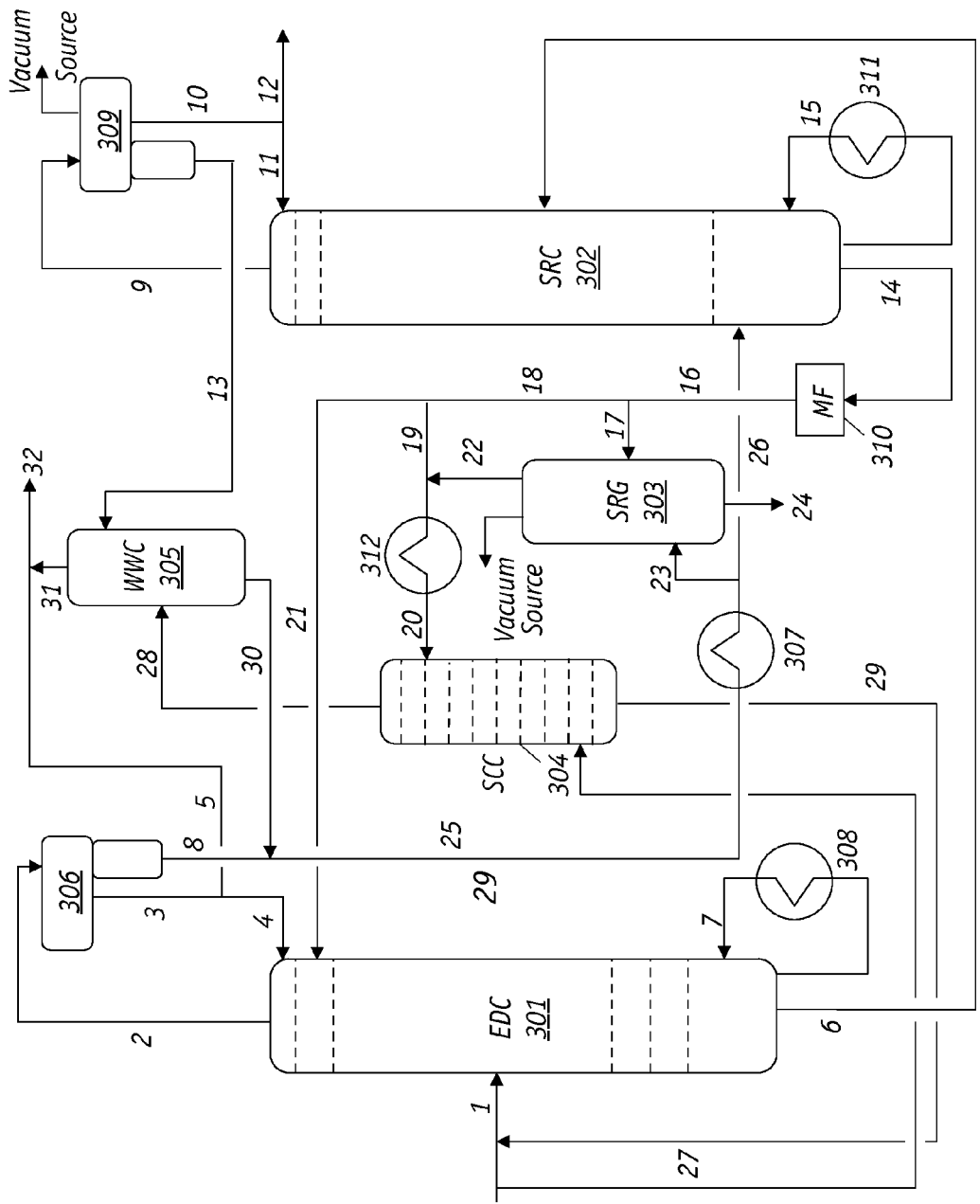
FIG. 1 depicts an extractive distillation process employing with a solvent clean-up system and a magnetically enhanced filter.

FIG. 1 is a schematic diagram of an ED process, for aromatic HCs recovery, which employs among other devices, an extractive distillation column (EDC) 301, solvent recovery column (SRC) 302, thermal solvent regenerator (SRG) 303, solvent clean-up column (SCC) 304, and water washing column (WCC) 305. Sulfolane with water is used as the selective solvent. A HC feed containing a mixture of aromatic and non-aromatic HCs is fed via line 1 to the middle portion of EDC 301, while a lean solvent from the bottom of SRC 302 is fed via lines 14, 16, 18, and 21 to near the top of EDC 301 below the overhead reflux entry point for line 4.

Non-aromatics vapor exiting the top of EDC 301 through line 2 is condensed in a condenser (not shown) and the condensate is transferred to an overhead receiver 306, which serves to effect a phase separation between the non-aromatic HCs and water phases. A portion of the non-aromatic HC phase is recycled to the top of EDC 301 as the reflux via lines 3 and 4 as a second portion is withdrawn as the raffinate product through line 5. The water phase from overhead receiver 306 in line 8 is combined with water in line 30 from WWC 305 and the mixture is transferred to a steam generator 307 via line 25 to form stripping steam that is introduced into SRC 302 via line 26 and into SRG 303 via line 23. The rich solvent stream containing the solvent, aromatics, and measurable levels of heavy HCs is withdrawn from the bottom of EDC 301. A portion of the rich solvent is heated in the reboiler 308 and recycled to the bottom of EDC 301 via line 7 to generate vapor stream in column, while the rest of the rich solvent is fed to the middle portion of SRC 302 through line 6.

Stripping steam when injected via line 26 into the lower portion of SRC 302 assists in the removal of aromatic HCs from the solvent. An aromatic concentrate, containing water and which is substantially free of solvent and non-aromatic HCs, is withdrawn through line 9 as an overhead vapor stream from SRC 302 and after being condensed in a condenser (not shown), the liquid is introduced into an overhead receiver 309 that serves to effect a phase separation between the aromatic HC phase and water phase. A portion of the aromatic HC phase from line 10 is recycled to the top of SRC 302 as the reflux via line 11, while the remaining portion is withdrawn as the aromatic HC product through line 12. The water phase is transferred through line 13 as the wash water to upper portion of WWC 305 from where solvent-free non-aromatic products are removed from the top via line 31.

In order to minimize the bottom temperature of SRC 302, receiver 309 is connected to a vacuum source to generate sub-atmospheric conditions in SRC 302. A lean solvent stream containing measurable amounts of heavy HCs is withdrawn from the bottom of SRC 302 through line 14. The main proportion thereof is recycled via lines 14, 16, 18 and 21 as the lean solvent feed to the upper portion of EDC 301 for extracting the aromatic HCs in the EDC. An inline magnetic filter 310 enhanced with a magnetic field (MF) is installed in the main lean solvent loop to remove the paramagnetic contaminants and sludge from the lean solvent. Suitable filters with magnets are described in US patent Publication Nos. 20090272702, 20100065504, 20120165551, and 20120228231 all to Yen, et al.

A minor portion of the lean solvent stream from the bottom of SRC 302 is diverted into SRG 303 via line 17 and steam is introduced into SRG 303 through line 23, at an entry point below the lean solvent feed entry point. To minimize the bottom temperature of SRG, 303 it is preferably operated under reduced pressure (vacuum). Another minor portion of the lean solvent is heated in the reboiler 311 and recycled to the bottom of SRC 302 via line 15.

Deteriorated solvent and polymeric sludge are removed from SRG 303 as a bottom stream through line 24 while regenerated solvent containing heavy HCs (with boiling points below the solvent's boiling point) and substantially all the stripping steam, are recovered as an overhead vapor stream 22. This vapor is combined with the split lean solvent from the bottom of SRC 302 via line 19, and the combined stream contains the solvent, measurable amounts of heavy HCs and substantially all the stripping steam from SRG 303, to form a mixture that is condensed and cooled in cooler 312 and then introduced via line 20 into the upper portion of SCC 304 below the location of solvent/HC interface. The HC phase from the top of SCC 304 is transferred through 28 into WWC 305.

A slip stream from HC feed stream of EDC 301 is fed to the lower portion of SCC 304 via line 27 to contact the lean solvent phase counter-currently as the displacement agent to squeeze out the heavy HCs and polymeric materials from the solvent phase.

In a preferred application of the ED process depicted in FIG. 1 using sulfolane as the solvent, the temperature of the overhead vapor 22 from SRG 303 typically ranges from 150° to 200° C., and preferably from 160° to 180° C., under a pressure of 0.1 to 10 atmospheres, and preferably of 0.1 to 0.8 atmospheres. The vapor is cooled in cooler 312 to a temperature approximately from 0 to 100° C., and preferably from 50 to 80° C. The EDC HC feed is split before heating and temperature of the slip stream to SCC 304 ranges from 0 to 100° C., preferably from 25 to 50° C. The HC feed-to-lean solvent feed weight ratio in SCC 304 is typically from 0.1 to 100, and preferably from 0.1 to 10. The contacting temperature in SCC 304 typically ranges 0° to 100° C., and preferably from 25 to 80° C. The operating pressure of SCC 304 typically ranges from 1 to 100 atmospheres, and preferably from 1 to 10 atmospheres. Operation conditions of SCC 304 are preferably selected to achieve the following objectives:

1. Benzene content in the HC phase is maintained a level so that benzene concentrate in the raffinate stream through line 32 (combination of lines 5 and 31) meets the product specification. For example, the benzene concentration in line 32 should below one volume percent for gasoline blending.

2. Content of heavy HC and polymeric material in the solvent phase withdrawn in line 29 is kept at a desirable range to maintain the solvent performance.

3. Since HC feed to the EDC or LLE column consists of 50% or more aromatics and is highly efficient in displacing the heavy HCs and polymeric materials from the lean solvent, only a minimum amount of HC feed is used to minimize the benzene concentration in HC phase of the SCC thereby not causing quality problem of the raffinate product of the ED or LLE process.

In the process of FIG. 1, instead of introducing the slip stream 27 as the displacement agent, an external stream comprising polar hydrocarbons (displacement agent) and having a boiling point range that at least partially matches that of the feed stream into the solvent cleanup zone is employed.

Figure 2:
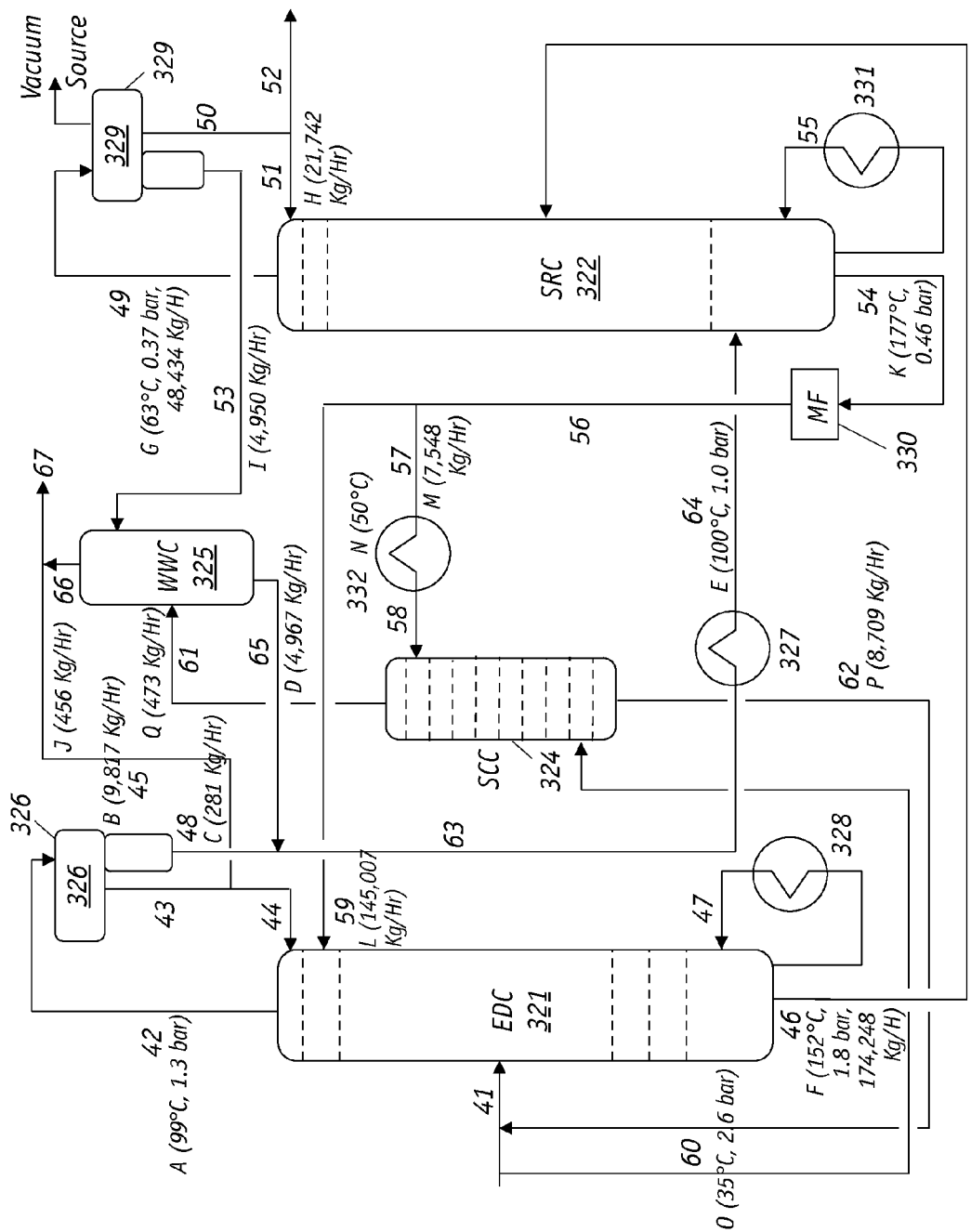
FIG. 2 depicts an extractive distillation process employing a solvent clean-up system and a magnetically enhanced filter but without a thermal solvent regenerator.

FIG. 2 illustrates an ED process for aromatic HCs recovery in which a lean solvent clean-up (SCC) 324 column using the EDC HC feed as the displacement agent and an inline filter 330 are employed to regenerate the solvent. The solvent regeneration scheme in this process does not employ a high temperature and energy intensive thermal solvent regenerator. This ED process employs, among other devices, an extractive distillation column (EDC) 321, solvent recovery column (SRC) 322, solvent clean-up column (SCC) 324, and water washing column (WCC) 325.

A HC feed containing a mixture of aromatic and non-aromatic HCs is fed via line 41 to the middle portion of EDC 321, while lean solvent in stream 59 is fed to near the top of EDC 321, below the overhead reflux entry point for line 44, for extracting the aromatic HCs in EDC 321. Again, the lean solvent from SRC 322 can be filtered with a magnet-enhanced filter 330 that removes iron rust particulates and other polymeric sludge that are paramagnetic in nature. Non-aromatics vapor exiting the top of EDC 321 through line 42 is condensed in a condenser (not shown) and the condensate is transferred to an overhead receiver 326, which serves to effect a phase separation between the non-aromatic HCs and the water phases. A portion of the non-aromatic HC phase in line 43 is recycled to the top of EDC 321 as the reflux via line 44 while a second portion is withdrawn as raffinate product through line 45. The water phase from the overhead receiver 326 in line 48 is combined with water in line 65 from the WWC and the mixture is transferred to a steam generator 327 via line 63 to form the stripping steam that is introduced into SRC 322 via line 64, which assists in the removal of aromatic HCs from the solvent. The rich solvent stream containing the solvent, aromatic HCs, and measurable amounts heavy HCs are withdrawn from the bottom of EDC 321. A portion of the rich solvent is heated in the reboiler 328 and recycled to the bottom of EDC 321 via line 47 to generate vapor stream in the column, while the rest of the rich solvent is fed to the middle portion of SRC 322 through line 46.

An aromatic concentrate, containing water and which is substantially free of solvent and non-aromatic HCs, is withdrawn through line 49 as an overhead vapor stream from SRC 322 and after being condensed in a condenser (not shown), the liquid is introduced into overhead receiver 329 which serves to effect a phase separation between the aromatic HC phase and the water phase. A portion of the aromatic HC phase from line 50 is recycled to the top of SRC 322 as the reflux via line 51, while the remaining portion is withdrawn as the aromatic HC product through line 52. The water phase is transferred through line 53 as the wash water to the upper portion of WWC 325 and the solvent-free HCs are removed from the top via line 66, which is combined with the EDC raffinate in line 45 to yield the raffinate product in line 67.

In order to minimize the bottom temperature of SRC 322, receiver 329 is connected to a vacuum source to generate sub-atmospheric conditions in SRC 322. A lean solvent stream containing measurable amounts of heavy HCs is withdrawn from the bottom of SRC 322. The majority proportion thereof is recycled through a magnetic enhanced filter 330 via lines 54, 56 and 59 to the upper portion of EDC 321 as the lean solvent feed. A minor portion of the lean solvent is diverted through line 57 and cooled in cooler 332 and then introduced via line 58 into the upper portion of SCC 324 below the location of solvent/HC interface. Another minor portion of the lean solvent is heated in reboiler 331 and recycled to the bottom of SRC 322 via line 55. A slip stream from HC feed stream of EDC 321 is fed to the lower portion of SCC 324 via line 60 to contact the lean solvent phase counter-currently as the displacement agent to squeeze out the heavy HCs and polymeric materials from the solvent phase.

The bottom stream from SCC 324, which contains essentially the purified solvent, most of the aromatic components in the slip EDC feed stream, especially benzene, and much reduced levels of heavy HCs and polymeric materials, is continuously withdrawn from lower portion of SCC 324 and introduced through line 62 as a part of HC feed to EDC 321, as a way to recycle the purified solvent into the solvent loop. The HC phase accumulated on the top of SCC 324 is removed periodically or continuously from the overhead of SCC 324 under interface level control to be fed via line 61 to WWC 325 to remove any solvent from the HC product, which is withdrawn from the top via line 66. The solvent clean-up operation can also be implemented in any other suitable continuous multi-stage contacting device, preferably one that is designed for counter-current extraction, such as multi-stage mixers/settlers, or other rotating-type contactors. In the absence of a thermal solvent regenerator, magnetic filter 330 in the lean solvent line between the SRC and EDC is critical for selectively removing paramagnetic species that are generated from the interaction of decomposed solvent with various solvent additives as well as the heavy HCs. Non-paramagnetic heavy HCs are removed in SCC 324 to keep the lean solvent clean at all times.

In a preferred application of the ED process depicted in FIG. 2 with sulfolane as the solvent, the split lean solvent stream from the bottom of SRC 322 via line 57 is cooled in cooler 332 before feeding to upper portion of SCC 324. The EDC HC feed is split before heating and fed to the lower portion of SCC 324. Operating conditions for cooler 332 and SCC 324 are typically the same as the corresponding units in the process shown in FIG. 1. Similarly, for the process of FIG. 2, an external stream as described previously can be employed instead of slip stream 60.

Figure 3:
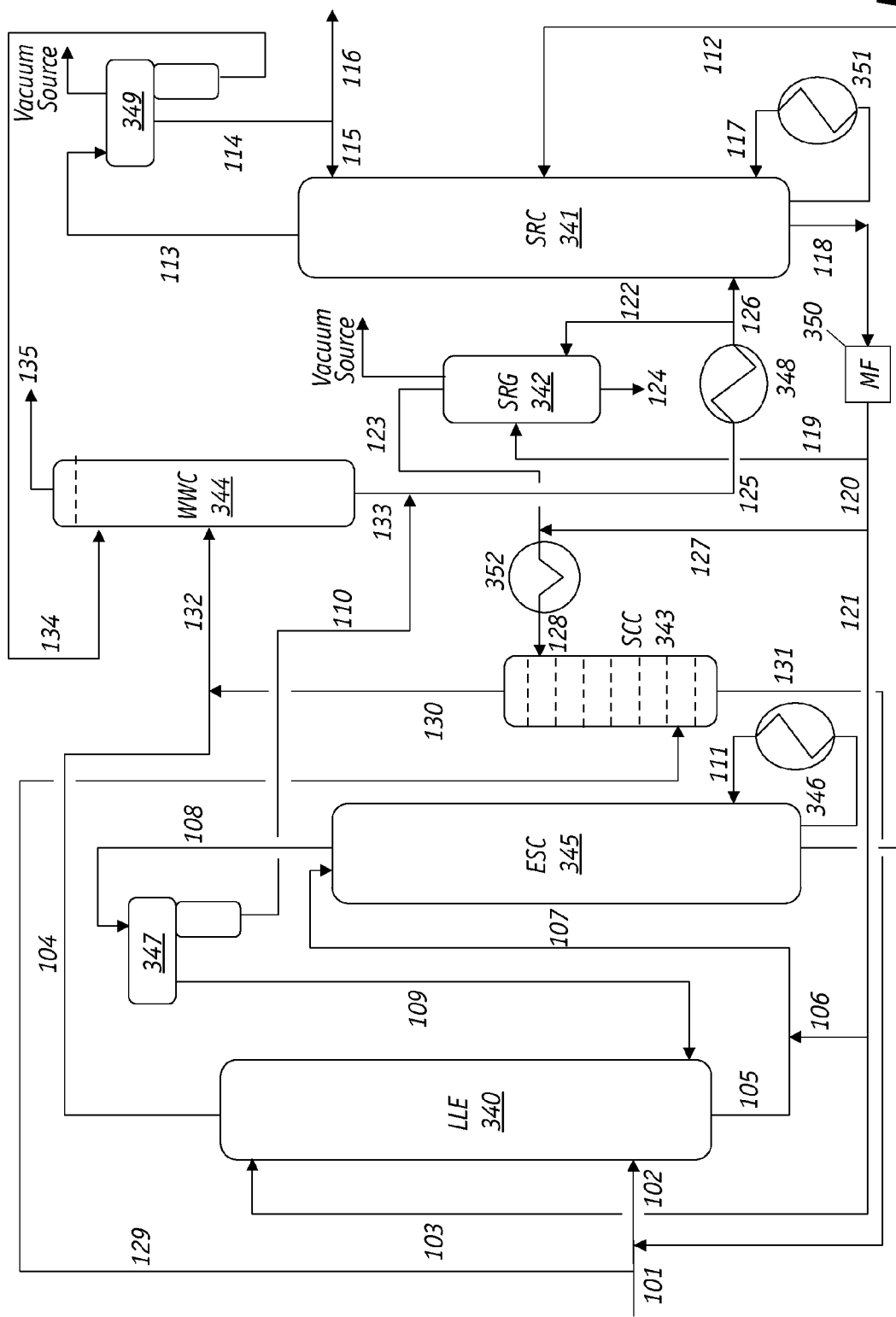
FIG. 3 depicts a liquid-liquid extraction process employing a solvent clean-up system and a magnetically enhanced filter.

FIG. 3 is a schematic diagram of a LLE process for aromatic HC recovery, which employs among other devices, a liquid-liquid extraction (LLE) column 340, solvent recovery column (SRC) 341, solvent regenerator (SRG) 342, solvent clean-up column (SCC) 343, water washing column (WCC) 344, and extractive stripper column (ESC) 345. HC feed containing a mixture of aromatics and non-aromatics is fed via lines 101 and 102 to the middle portion of LLE column 340, while lean solvent is introduced near the top of LLE column 340 via line 103 to counter-currently contact the HC feed. The aromatic HCs in the feed typically comprise benzene, toluene, ethylbenzene, xylenes, $C_9^+$ aromatics, and mixtures thereof, and the non-aromatic hydrocarbons typical comprise $C_5$ to $C_9^+$ paraffins, naphthenes, olefins, and mixtures thereof.

A raffinate phase containing essentially the non-aromatics with a minor amount of solvent is withdrawn from the top of LLE column 340 as stream 104 and is fed to a middle portion of WWC 344 via line 132. An extract phase from the bottom of LLE column 340 in line 105 is mixed with a secondary lean solvent from line 106; the combined stream 107 is fed to the top of ESC 345.

The vapor flow through ESC 345 is generated by the action of reboiler 346, whereby a portion of the rich solvent in the bottom is recycled to ESC 345 via line 111 through reboiler 346 which is normally heated by steam at a rate that is sufficient to control the column bottom temperature, the overhead stream composition and the flow rate. Overhead vapor exiting the top of ESC 345 is condensed in a cooler (not shown) and the condensate is transferred via line 108 to an overhead receiver 347, which serves to effect a phase separation between the HC and the water phases. The HC phase, containing the non-aromatics and up to 30-40% benzene and heavier aromatics, is recycled to the lower portion of LLE column 340 as reflux via line 109. The water phase is transferred via lines 110 and 125 to steam generator 348 to generate stripping steam for SRC 341. Rich solvent consisting of the solvent, aromatics that are free of non-aromatics, and measurable amounts of heavy HCs and polymeric materials is withdrawn from the bottom of ESC 345 and transferred to the middle portion of SRC 341 via line 112. Stripping steam is injected from steam generator 348 via line 126 into the lower portion of SRC 341 to assist the removal of aromatic HCs from the solvent. An aromatic concentrate, containing water and being substantially free of solvent and non-aromatic hydrocarbons, is withdrawn as an overhead vapor stream from SRC 341 and introduced into an overhead receiver 349 via line 113 after being condensed in a cooler (not shown). In order to minimize the bottom temperature of SRC 341, receiver 349 is connected to a vacuum source to generate sub-atmospheric conditions in SRC 341.

Overhead receiver 349 serves to effect a phase separation between the aromatic HC and the water phases. A portion of the aromatic HC phase in line 114 is recycled to the top of SRC 341 as reflux via line 115, while the remainder portion is withdrawn as aromatic HC product through line 116. The water phase that accumulates in the water leg of overhead receiver 349 is fed via line 134 to WWC 344 as wash water at a location below the interface between the HC phase and the water phase near the top of WWC 344. The solvent is removed from the LLE raffinate and the HC phase of SCC 343 through a counter-current water wash and the solvent-free HCs, which accumulate in the HC phase of WWC 344, are then withdrawn from the top of the column as solvent-free raffinate product through line 135. A water phase, containing the solvent, exits through line 133 from the bottom of WWC 344 and is combined with line 110, that is the water phase from overhead receiver 347, and is fed to steam generator 348 via line 125 where it is transformed into stripping steam that is introduced into SRC 341 via line 126 and into SRG 342 via line 122.

A greater proportion of the lean solvent from the bottom of SRC 341 is recycled through a magnetic enhanced filter 350 via lines 118, 120, 121 and 103 as a lean solvent feed that is supplied to the upper portion of LLE column 340 for extracting the aromatic HCs in LLE column 340. A split stream of the lean solvent from SRC 341 bottom is diverted into SRG 342 via line 119 and steam is introduced into SRG 342 through line 122, at a location below the lean solvent feed entry point. A portion of the lean solvent is heated in reboiler 351 and recycled to the bottom of SRC 341 via line 117. Deteriorated solvent and polymeric sludge are removed as a bottom stream through line 124, while the regenerated solvent and substantially all the stripping steam, are recovered as an overhead stream 123. A mixture formed of this vapor in line 123 and a split lean solvent from the bottom of SRC 341 in line 127, containing the solvent, a measurable amount of heavy HCs and substantially all the stripping steam from SRG 342, is condensed and cooled in cooler 352 and is introduced via line 128 into the upper portion of SCC 343 below the location of solvent/HC interface.

A slip stream from the HC feed to LLE column 340 is fed to the lower portion of SCC 343 via line 129 as the displacement agent to contact the solvent phase counter-currently to squeeze out the heavy HCs and polymeric materials from the solvent phase into the HC phase in SCC 343. Optionally, any desulfurized light HC mixture, preferably containing polar (aromatic) HCs can be used effectively as the displacement agent.

Solvent phase containing essentially purified solvent, most of the aromatics components in the slip HC feed stream (the displacement agent), and substantially reduced levels of heavy HCs and polymeric materials is continuously withdrawn from the bottom of SCC 343 and introduced through lines 131 into LLE column 340 as a part of the HC feed, as a way to recycle the purified solvent into the solvent loop. The HC phase accumulates continuously at the top of SCC 343 and is removed periodically or continuously from the overhead of SCC 343 via lines 130 under interface level control, which is then mixed with the raffinate stream from the overhead of LLE column 340 and fed via line 132 to WWC 344. The solvent clean-up operation can be implemented with other suitable continuous multi-stage contacting device, preferably one that is designed for counter-current extraction, such as multi-stage mixers/settlers, or other rotating type contactors.

In a preferred application of the LLE process that is depicted in FIG. 3 and preferably with sulfolane as the solvent, the operating conditions of SRG 342, cooler 352, and SCC 343 are the same those of the corresponding units for the process shown in FIG. 1. Similarly, an external stream can be employed instead of slip stream 129.

Figure 4:
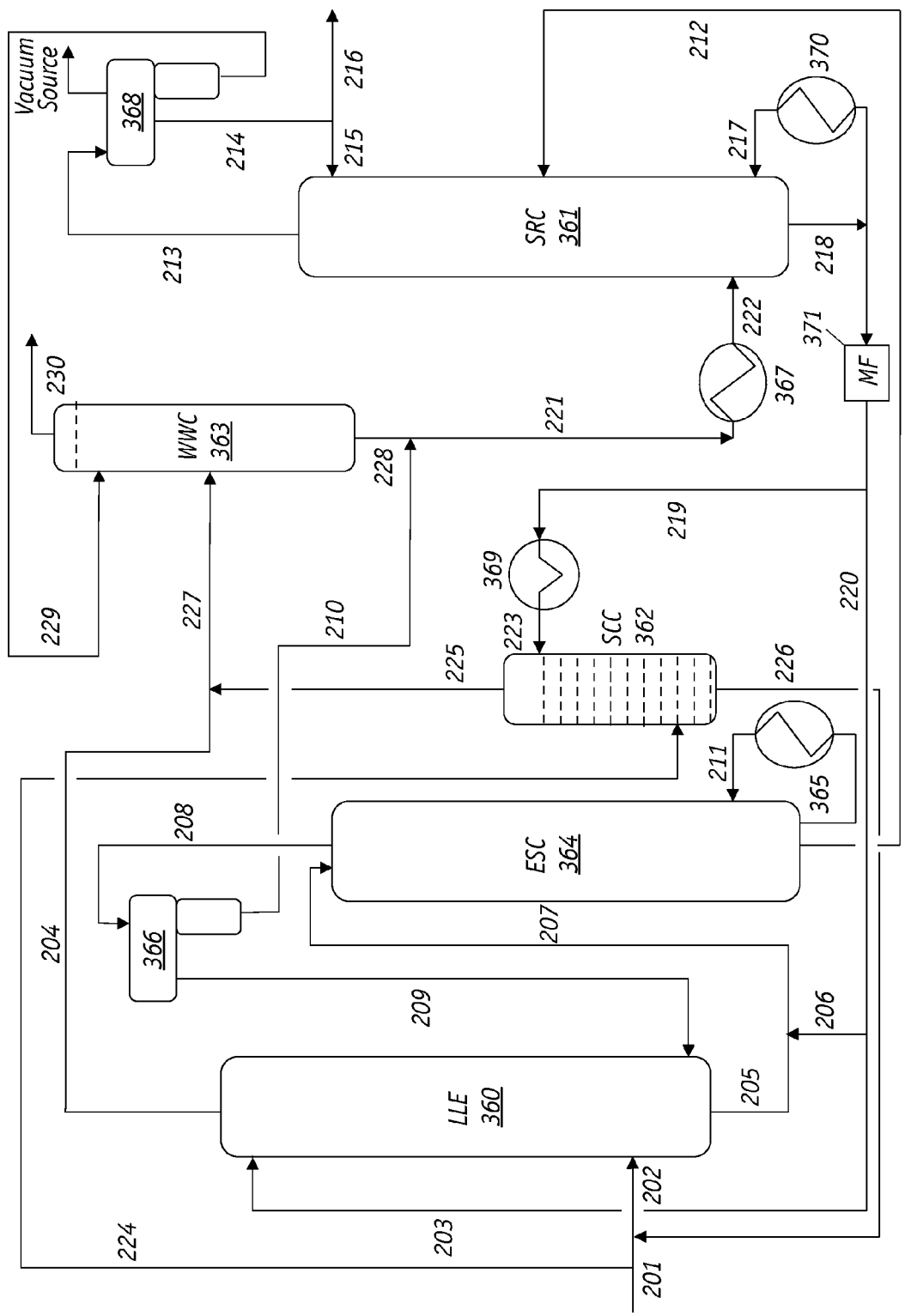
FIG. 4 depicts a liquid-liquid extraction process employing solvent clean-up system and a magnetically enhanced filter but without a thermal solvent regenerator.

FIG. 4 illustrates a LLE process for aromatic HCs recovery from the mixture containing aromatic HCs and non-aromatic HCs, in which a solvent clean-up column (SCC) using HC feed to the LLE column as the displacement agent and an inline filter enhanced with magnetic field (MF) are employed to regenerate the lean solvent. The high temperature and energy intensive solvent regenerator is not required.

The process employs liquid-liquid extraction (LLE) column 360, solvent recovery column (SRC) 361, solvent clean-up column (SCC) 362, water washing column (WCC) 363, and extractive stripper column (ESC) 364. HC feed containing a mixture of aromatic and non-aromatics is fed via lines 201 and 202 to the middle portion of LLE column 360, while lean solvent is introduced near the top of LLE column 360 via line 203 to counter-currently contact the HC feed. A raffinate phase in stream 204 containing essentially the non-aromatics with minor amounts of solvent is withdrawn from the top of LLE column 360 and fed to a middle portion of WWC 363 via line 227. An extract phase is transferred from the bottom of LLE column 360 via line 205 and is mixed with a secondary lean solvent from line 206; the combined stream 207 is fed to the top of ESC 364.

The vapor flow through ESC 364 is generated by the action of reboiler 365, whereby a portion of the rich solvent in bottom is recycled to ESC 364 via line 211 through reboiler 365, which is normally heated by steam at a rate that is sufficient to control the column bottom temperature, the overhead stream composition and the flow rate. Overhead vapor exiting the top of ESC 364 is condensed in a cooler (not shown) and the condensate is transferred via line 208 to an overhead receiver 366, which serves to effect a phase separation between the HC and the water phases. The HC phase, containing the non-aromatics and up to 30-40% benzene and heavier aromatics, is recycled to the lower portion of LLE column 360 as reflux via line 209. The water phase is transferred via lines 210 and 221 to steam generator 367 to generate stripping steam for SRC 361. Rich solvent consisting of the solvent, purified aromatics, and measurable amounts of heavy HCs and polymeric materials is withdrawn from the bottom of ESC 364 and transferred to the middle portion of SRC 361 via line 212. Stripping steam is injected from steam generator 367 via line 222 into the lower portion of SRC 361 to assist the removal of aromatic HCs from the solvent. An aromatic concentrate, containing water and being substantially free of solvent and non-aromatics, is withdrawn as an overhead vapor stream from SRC 361 and introduced into overhead receiver 368 via line 213 after being condensed in a cooler (not shown). In order to minimize the bottom temperature of SRC 361, receiver 368 is connected to a vacuum source to generate sub-atmospheric conditions in SRC 361.

Overhead receiver 368 serves to effect a phase separation between the aromatic HC and the water phases. A portion of the aromatic HC phase in line 214 is recycled to the top of SRC 361 as reflux via line 215, while the remainder portion is withdrawn as aromatic HC product through line 216. The water phase that accumulates in the water leg of overhead receiver 368 is fed via line 229 to WWC 363 as wash water at a location below the interface between the HC and the water phases near the top of WWC 363. Solvent is removed from the LLE raffinate and the HC phase of SCC 362 through a counter-current water wash to yield solvent-free HC phase, which is then withdrawn from the top of WWC 363 as the raffinate product through line 230. A water phase, containing the solvent, is withdrawn through line 228 from the bottom of WWC 363 and combined with line 210 that is the water phase from receiver 366. The mixture is fed to steam generator 367 via line 221 where it is transformed into stripping steam and introduced into SRC 361 via line 222.

A split stream 219 of the lean solvent from SRC 361 in line 218 is cooled in cooler 369 and then introduced via line 223 into the upper portion of SCC 362 below the location of the solvent HC interface. A portion of the lean solvent is heated in the reboiler 370 and recycled to the bottom of SRC 361 via line 217. Preferably, the majority of the lean solvent exiting from the bottom of the SRC is transferred into LLE column 360 via lines 218, 220, and 203.

A split stream from HC feed to LLE column 360 is fed via line 224 to a lower portion of SCC 362, as a displacement agent, to contact the solvent phase and squeeze out the heavy HCs and polymeric materials from the solvent phase into the HC phase in SCC 362. A solvent phase, that contains essentially purified solvent, most of the aromatic components in said split stream (the displacement agents), and substantially reduced levels of heavy HCs and polymeric materials, is continuously withdrawn from lower portion of SCC 362 and introduced through lines 226 into LLE column 360 as a part of the HC feed, as a way to recycle the purified solvent into the solvent loop. A magnetic filter 371 is preferably installed in the main lean recycle line between SRC 361 and LLE column 360 to remove the paramagnetic contaminants.

The HC phase which accumulates continuously at the top of SCC 362 and is removed periodically or continuously from the overhead of SCC 362 via line 225 under interface level control, which is then mixed with the raffinate stream from the overhead of LLE column 360 before being fed via line 227 to WWC 363 to remove solvent from the raffinate product withdrawn from the top of WWC 363 via line 230. In a preferred application of the LLE process that is depicted in FIG. 4, sulfolane is the solvent and the operating conditions of cooler 369 and SCC 362 are comparable to the corresponding units of the process shown in FIG. 1. Finally, instead of slip stream 224, an external stream as described above is introduced into the solvent cleanup zone as the displacement agent.

EXAMPLE

Computer simulation modeling of extractive distillation processes for recovering aromatic HCs using representative commercial data demonstrated the feasibility of the present invention. Specifically, this example demonstrates that detectable heavy HCs in the lean solvent generated from the bottom of the SRC are displaced from the lean solvent by the HC feedstock that is fed to the EDC or LLE column. Referring to the process shown in FIG. 2, approximately 39,097 Kg/Hr of HC feedstock, containing 55.4 wt % $C_6$-$C_8$ aromatic HCs at 112° C. and 5.0 bar, is fed to the middle portion of the EDC via line 41, while roughly 145,007 Kg/Hr of sulfolane solvent at 95° C. and 2 bar containing 0.4 wt % water in stream 59 is fed to near the top of the EDC, below the overhead reflux entry point from line 44, for extracting the aromatic HCs in the EDC. The mass flow rates of species in selected streams are summarized in Table 1.

ing parameters for streams or devices that are identified by the reference character numbers 42, 45, 48, 65, 64, 46, 49, 51, 53, 66, 54, 59, 57, 332, 60, 62, and 61, are set forth in FIG. 2 adjacent to the letter designations A through Q, respectively. Under these process conditions, 50% of the aromatic HC phase from line 50 is recycled at a rate of 21,742 Kg/Hr to the top of the SRC as the reflux via line 51 and the remaining portion is withdrawn as the aromatic HC product through line 52.

To demonstrate capability of the HC feedstock for displacing heavy HCs in the lean solvent, material balances of the heavy HCs in different streams around the solvent clean-up column (SCC) are summarized in Table 2:

TABLE 2

HC Feed (Displacement Agent)/Lean Solvent = 0.216 (weight)
Displacement Temperature: 35° C. to 50° C.

| | (Unit: Kg/Hr) | | | |
|---|---|---|---|---|
| | In | Out | | |
| | Stream No. | | | |
| | 58 | 60 | 61 | 62 |
| $C_{10}^+$ Non-Aromatics | 8.521 | 0.405 | 8.055 | 0.871 |
| $C_{10}^+$ Aromatics | 10.518 | 0.200 | 3.992 | 6.726 |
| Total | 19.039 | 0.605 | 12.047 | 7.597 |

As shown in Table 2, under a HC feed (displacement agent)-to-lean solvent weight ratio of only 0.2 and only one theoretical separation stage, the total heavy HCs in the lean solvent is reduced from 19.039 Kg/Hr (stream 58) to 7.597 Kg/Hr (stream 62), which is a 60 wt % reduction in just one pass, wherein, $C_{10}^+$ non-aromatics and $C_{10}^+$ aromatics are reduced 89.8 and 36.1 wt %, respectively. This shows that

TABLE I

| | (Flow Rate: Kg/Hr) | | | | | | | | |
|---|---|---|---|---|---|---|---|---|---|
| Stream No. | 41 | 59 | 45 | 46 | 58 | 60 | 61 | 62 | 67 |
| $nC_5$ | 102 | 0 | 102 | 0 | 0 | 5.4 | 2.8 | 2.6 | 105 |
| $iC_5$ | 70.0 | 0 | 70.0 | 0 | 0 | 3.7 | 1.9 | 1.8 | 71.9 |
| $CyC_5$ | 645 | 0 | 645 | 0 | 0 | 33.6 | 13.1 | 20.5 | 658 |
| $nC_6$ | 1852 | 0 | 1852 | 0 | 0 | 97.6 | 61.1 | 36.5 | 1913 |
| $iC_6$ | 1732 | 0 | 1732 | 0 | 0 | 91.8 | 67.4 | 24.4 | 1792 |
| $CyC_6$ | 2697 | 0 | 2697 | 0 | 0 | 141 | 69.9 | 71.2 | 2767 |
| Benzene | 12043 | 0 | 42.2 | 12001 | 0 | 617 | 55.0 | 562 | 101 |
| $nC_7$ | 421 | 0 | 421 | 0 | 0 | 22.3 | 16.0 | 6.2 | 437 |
| $iC_7$ | 392 | 0 | 392 | 0 | 0 | 20.8 | 15.2 | 5.5 | 407 |
| $CyC_7$ | 1024 | 0 | 1024 | 0 | 0 | 53.9 | 32.3 | 21.6 | 1057 |
| Toluene | 5821 | 0 | 0.1 | 5821 | 0 | 299 | 39.1 | 260 | 39.8 |
| $nC_8$ | 177 | 0 | 177 | 0 | 0 | 9.5 | 7.5 | 1.9 | 185 |
| $iC_8$ | 272 | 0 | 272 | 0 | 0 | 14.5 | 11.5 | 3.0 | 284 |
| $CyC_8^+$ | 208 | 0 | 199 | 9.6 | 0 | 11.0 | 7.9 | 3.2 | 207 |
| $C_8$ Aromatics | 3790 | 12.8 | 0 | 3790 | 0.7 | 195 | 36.9 | 159 | 37.1 |
| $nC_9$ | 35.6 | 0 | 5.3 | 30.3 | 0 | 1.9 | 1.6 | 0.3 | 6.7 |
| $iC_9$ | 143 | 0 | 139 | 4.4 | 0 | 7.6 | 6.5 | 1.1 | 145 |
| $CyC_9$ | 124 | 0 | 33.1 | 87.3 | 0 | 6.6 | 5.1 | 1.5 | 33.1 |
| $C_9$ Aromatics | 8.1 | 4.1 | 0 | 8.1 | 0.2 | 0.4 | 0.2 | 0.4 | 0.2 |
| $nC_{10}^+$ | 8.4 | 164 | 1.2 | 172 | 8.5 | 0.4 | 8.1 | 0.9 | 9.2 |
| $C_{10}^+$ Aromatics | 10.4 | 202 | 7.9 | 213 | 10.5 | 0.2 | 4.0 | 6.7 | 11.9 |
| Sulfolane | 7486 | 143979 | 4.1 | 151474 | 7495 | 0 | 9.1 | 7486 | 4.1 |
| Water | 33.6 | 646 | 1.9 | 637 | 33.6 | 0 | 0 | 33.6 | 2.1 |
| Total | 39097 | 145007 | 9817 | 174248 | 7548 | 1633 | 473 | 8709 | 10273 |

In the above table, the prefix "n" refers to straight chain aliphatics, "i" refers to branched aliphatics, and "Cy" refers to cyclic aliphatics. Selected process flow rates and operatthe HC feedstock to the EDC is a very effective displacement agent for removing the heavy HCs from the lean solvent.

Since the HC feedstock contains approximately 30 wt % benzene, it is particularly preferred that the benzene content in the raffinate product in line 67 (combination of lines 45 and 66 of FIG. 2) meets product specifications, when the HC feedstock is used as the displacement agent for removing the heavy HCs from the lean solvent. As shown in Table 1, the benzene content in the raffinate product (in line 67) is 0.98 wt %, which meets the requirement for gasoline blending (<1.0 wt % benzene). Operation of SCC 324 can be adjusted to yield the raffinate product having different benzene contents in order to meet the specification for various applications.

What is claimed is:

1. A method of recovering a polar hydrocarbon selective solvent substantially free of hydrocarbons and other impurities from a solvent-rich stream containing selective solvent, measurable amounts of heavy hydrocarbons, and polymeric materials, which method comprises the steps of:
(a) providing a feed stream containing polar and less polar hydrocarbons wherein the feed stream contains one or more petroleum products that is selected from reformate, pyrolysis gasoline, coke oven oil and coal tar;
(b) introducing the feed stream into an extraction zone, which includes an extractive distillation column or a liquid-liquid extraction column, to yield (i) a less polar hydrocarbon stream and a first water stream and (ii) a polar hydrocarbon stream, lean a solvent stream and a second water stream; and
(c) introducing a portion of the lean solvent stream into a solvent cleanup zone at a first location and introducing a slip stream from the feed stream into the solvent cleanup zone at a second location whereby aromatic hydrocarbons in the slip stream displace heavy hydrocarbons from the lean solvent stream thereby yielding a solvent phase that is introduced into the extraction zone and a hydrocarbon phase that contains the displaced heavy hydrocarbons.

2. The method of claim 1, wherein the polar hydrocarbons are aromatic and the less polar hydrocarbons are paraffinic, naphthenic, and olefinic.

3. The method of claim 1 wherein the solvent is selected from the group consisting of sulfolane, alkyl-sulfolane, N-formyl morpholine, N-methyl pyrrolidone, tetraethylene glycol, triethylene glycol, diethylene glycol, and mixtures thereof.

4. The method of claim 1 wherein the solvent cleanup zone is an extraction column that is selected from the group consisting of (i) columns equipped with trays, packings or rotating discs, (ii) a multi-stage mixer/settler and (iii) pulse column.

5. The method of claim 1 wherein the solvent cleanup zone is a countercurrent extraction column.

6. The method of claim 1 wherein step (b) comprises the steps of:
(i) introducing the feed stream into a middle portion of the extractive distillation column (EDC) and introducing a solvent-rich stream into an upper portion of the EDC as a selective solvent feed;
(ii) recovering a water-containing, less polar hydrocarbon-rich stream from a top of the EDC and withdrawing a first solvent-rich stream containing solvent and polar hydrocarbons from a bottom of the EDC;
(iii) introducing the first solvent-rich stream into the middle portion of a solvent recovery column (SRC), recovering a polar hydrocarbon-rich stream, that is substantially free of solvent and less polar hydrocarbons, from a top of the SRC, and removing a second solvent-rich stream from a bottom of the SRC;
(iv) introducing a first portion of the second solvent-rich stream into the upper portion of the EDC in step (i) as the selective solvent feed; and
(v) cooling a second portion of the second solvent-rich stream in step (iii) and introducing the cooled second portion of the solvent-rich stream into an upper portion of the solvent cleanup zone to form the solvent phase; wherein step (c) comprises the steps of:
(vi) introducing the slip stream into a lower portion of the solvent cleanup zone, as a heavy hydrocarbon displacement agent, to squeeze out heavy hydrocarbons and polymeric materials from the solvent phase into a hydrocarbon phase; and
(vii) withdrawing an accumulated hydrocarbon phase containing heavy hydrocarbons and polymeric materials from an upper portion of the solvent cleanup zone, and recovering the solvent phase containing solvent and polar hydrocarbons and substantially reduced levels of heavy hydrocarbons and polymeric materials, from a lower portion of the solvent cleanup zone; and, the method further comprises the step of: (viii) introducing the solvent phase from the solvent cleanup zone into a middle portion of the EDC as part of a hydrocarbon feed to recycle purified solvent into a solvent loop.

7. The method of claim 6 further comprising filtering the first portion of the second solvent-rich stream with an in-line filter that is enhanced with a magnetic field before the first portion of the second solvent-rich stream enters the upper portion of the EDC.

8. The method of claim 6 wherein the EDC is operated under such conditions so as to keep substantially all $C_9^+$ hydrocarbons in the first solvent-rich stream in order to maximize benzene recovery.

9. The method of claim 6 wherein the SRC is operated under such conditions as to strip only $C_8$ and lighter hydrocarbons from the first solvent-rich stream and keep substantially all $C_9$ and heavier hydrocarbons in the second solvent-rich stream.

10. The method of claim 6 wherein step (iv) comprises: introducing a greater portion of the second solvent-rich stream into an upper portion of the EDC and introducing a first minor portion of the second solvent-rich stream into an upper portion of a thermal solvent regeneration zone, recovering a third solvent-rich stream containing solvent, water, and hydrocarbons and other compounds having boiling points that are below that of the solvent, from a top of the solvent regeneration zone, and removing heavy sludge from a lower portion of the solvent regeneration zone; and wherein step (v) comprises:
cooling a mixture that comprises the third solvent-rich stream in step (iv) and a second minor portion of the second solvent-rich stream in step (iii) and introducing the mixture into an upper portion of the solvent cleanup zone to form the solvent phase.

11. The method of claim 6 wherein the solvent is sulfolane.

12. The method of claim 6 wherein the solvent is N-formyl morpholine.

13. The method of claim 1 wherein step (b) comprises the steps of:
(i) introducing the feed stream into a middle portion of a liquid-liquid extraction (LLE) column and introducing a solvent-rich stream into an upper portion of the LLE column as a selective solvent feed;

(ii) recovering a water-containing, less polar hydrocarbon-rich stream from a top of the LLE column and withdrawing the first solvent-rich stream containing solvent, polar hydrocarbons and minor amounts of less polar hydrocarbons from a bottom of the LLE column;

(iii) introducing a mixture comprising the first solvent-rich stream and a minor portion of a third solvent-rich stream from a bottom of a solvent recovery column (SRC) into an upper portion of an extractive stripping column (ESC), recovering a hydrocarbon-rich vapor, which contains less polar hydrocarbons and a significant amount of benzene and heavier aromatics, and which is condensed and recycled to a lower portion of LLE column as reflux, and withdrawing a second solvent-rich stream containing solvent and polar hydrocarbons, which is substantially free of less polar hydrocarbons, from a bottom of the ESC;

(iv) introducing the second solvent-rich stream in step (iii) into a middle portion of the SRC, withdrawing a polar hydrocarbon-rich stream, which is substantially free of solvent and less polar hydrocarbons, from a top of the SRC, and removing a third solvent-rich stream from the bottom of the SRC;

(v) introducing a major portion of the third solvent-rich stream into the upper portion of the LLE column in step (i) as the selective solvent feed; and (vi) cooling a minor portion of the third solvent-rich stream in step (iv) and introducing the cooled minor portion of the third solvent-rich stream into an upper portion of a solvent cleanup zone to form the solvent phase; wherein step (c) comprises:

(vii) introducing the slip stream into a lower portion of the solvent cleanup zone, as a heavy hydrocarbon displacement agent, to squeeze out heavy hydrocarbons and polymeric materials from the solvent phase into a hydrocarbon phase; and (viii) withdrawing an accumulated hydrocarbon phase containing heavy hydrocarbons and polymeric materials from an upper portion of the solvent clean-up zone and recovering the solvent phase containing solvent and polar hydrocarbons and having substantially reduced levels of heavy hydrocarbons and polymeric materials, from a lower portion of the solvent clean-up zone; and the method further comprises:

(ix) introducing the solvent phase from the solvent clean-up zone in step (viii) into a middle portion of the LLE column in step (i) as part of a hydrocarbon feed to recycle purified solvent into a solvent loop.

14. The method of claim 13 wherein step (v) comprises:
introducing a major portion of the third solvent-rich stream into the upper portion of the LLE column in step (i) and introducing a first minor portion of the third solvent-rich stream into an upper portion of a high-temperature thermal solvent regeneration zone, recovering a fourth solvent-rich stream containing solvent, water, and hydrocarbons and other compounds having boiling points that are below that of the solvent, from a top of the solvent regeneration zone, and removing heavy sludge from a lower portion of the solvent regeneration zone; and wherein step (vi) comprises:
cooling a mixture comprising the fourth solvent-rich stream in step (v) and a second minor portion of the third solvent-rich stream in step (iv) and introducing the mixture into an upper portion of the solvent cleanup zone to form the solvent phase.

15. The method of claim 1 wherein the feed stream contains one or more petroleum products that is selected from reformate and pyrolysis gasoline.

16. A method of recovering a polar hydrocarbon selective solvent substantially free of hydrocarbons and other impurities from a solvent-rich stream containing selective solvent, measurable amounts of heavy hydrocarbons, and polymeric materials, which method comprises the steps of:

(a) providing a feed stream containing polar and less polar hydrocarbons wherein the feed stream contains one or more petroleum products that is selected from reformate, pyrolysis gasoline, coke oven oil and coal tar;

(b) introducing the feed stream into an extraction zone, which includes an extractive distillation column or a liquid-liquid extraction column, to yield (i) a less polar hydrocarbon stream and a first water stream and (ii) a polar hydrocarbon stream, a lean solvent stream and a second water stream; and (c) introducing a portion of the lean solvent stream into a solvent cleanup zone at a first location and introducing an external stream a desulfurized light hydrocarbon mixture comprising polar hydrocarbons and having a boiling point range that at least partially overlaps that of the feed stream into the solvent cleanup zone whereby the polar hydrocarbons in the external stream displace heavy hydrocarbons from the lean solvent stream thereby yielding a solvent phase that is introduced into the extraction zone and a hydrocarbon phase that contains the displaced heavy hydrocarbons.

17. The method of claim 16 wherein the polar hydrocarbons are aromatic and the less polar hydrocarbons are paraffinic, naphthenic, and olefinic.

18. The method of claim 16 wherein the solvent is selected from the group consisting of sulfolane, alkylsulfolane, N-formyl morpholine, N-methyl pyrrolidone, tetraethylene glycol, triethylene glycol, diethylene glycol, and mixtures thereof.

19. The method of claim 16 wherein the solvent cleanup zone is an extraction column that is selected from the group consisting of (i) columns equipped with trays, packings or rotating discs, (ii) a multi-stage mixer/settler and (iii) pulse column.

20. The method of claim 16 wherein the solvent cleanup zone is a countercurrent extraction column.

21. The method of claim 16 wherein step (b) comprises the steps of:

(i) introducing the feed stream into a middle portion of the extractive distillation column (EDC) and introducing a solvent-rich stream into an upper portion of the EDC as a selective solvent feed;

(ii) recovering a water-containing, less polar hydrocarbon-rich stream from a top of the EDC and withdrawing a first solvent-rich stream containing solvent and polar hydrocarbons from a bottom of the EDC;

(iii) introducing the first solvent-rich stream into the middle portion of a solvent recovery column (SRC), recovering a polar hydrocarbon-rich stream, that is substantially free of solvent and less polar hydrocarbons, from a top of the SRC, and removing a second solvent-rich stream from a bottom of the SRC;

(iv) introducing a first portion of the second solvent-rich stream into the upper portion of the EDC in step (i) as the selective solvent feed; and (v) cooling a second portion of the second solvent-rich stream in step (iii) and introducing the cooled second portion of the solvent-rich stream into an upper portion of the solvent cleanup zone to form the solvent phase; wherein step (c) comprises the steps of:

(vi) introducing the external stream into a lower portion of the solvent cleanup zone, as a heavy hydrocarbon displacement agent, to squeeze out heavy hydrocarbons and polymeric materials from the solvent phase into a hydrocarbon phase; and (vii) withdrawing an accumulated hydrocarbon phase containing heavy hydrocarbons and polymeric materials from an upper portion of the solvent cleanup zone, and recovering the solvent phase containing solvent and polar hydrocarbons and substantially reduced levels of heavy hydrocarbons and polymeric materials, from a lower portion of the solvent cleanup zone; and, the method further comprises the step of: (viii) introducing the solvent phase from the solvent cleanup zone into a middle portion of the EDC as part of a hydrocarbon feed to recycle purified solvent into a solvent loop.

22. The method of claim 21 further comprising filtering the first portion of the second solvent-rich stream with an in-line filter that is enhanced with a magnetic field before the first portion of the second solvent-rich stream enters the upper portion of the EDC.

23. The method of claim 21 wherein the EDC is operated under such conditions so as to keep substantially all $C_9^+$ hydrocarbons in the first solvent-rich stream in order to maximize benzene recovery.

24. The method of claim 21 wherein the SRC is operated under such conditions as to strip only $C_8$ and lighter hydrocarbons from the first solvent-rich stream and keep substantially all $C_9$ and heavier hydrocarbons in the second solvent-rich stream.

25. The method of claim 21 wherein step (iv) comprises:
introducing a greater portion of the second solvent-rich stream into an upper portion of the EDC and introducing a first minor portion of the second solvent-rich stream into an upper portion of a thermal solvent regeneration zone, recovering a third solvent-rich stream containing solvent, water, and hydrocarbons and other compounds having boiling points that are below that of the solvent, from a top of the solvent regeneration zone, and removing heavy sludge from a lower portion of the solvent regeneration zone; and wherein step (v) comprises:
cooling a mixture that comprises the third solvent-rich stream in step (iv) and a second minor portion of the second solvent-rich stream in step (iii) and introducing the mixture into an upper portion of the solvent cleanup zone to form the solvent phase.

26. The method of claim 21 wherein the solvent is sulfolane.

27. The method of claim 21 wherein the solvent is N-formyl morpholine.

28. The method of claim 16 wherein step (b) comprises the steps of:
(i) introducing the feed stream into a middle portion of a liquid-liquid extraction (LLE) column and introducing a solvent-rich stream into an upper portion of the LLE column as a selective solvent feed;
(ii) recovering a water-containing, less polar hydrocarbon-rich stream from a top of the LLE column and withdrawing the first solvent-rich stream containing solvent, polar hydrocarbons and minor amounts of less polar hydrocarbons from a bottom of the LLE column;

(iii) introducing a mixture comprising the first solvent-rich stream and a minor portion of a third solvent-rich stream from a bottom of a solvent recovery column (SRC) into an upper portion of an extractive stripping column (ESC), recovering a hydrocarbon-rich vapor, which contains less polar hydrocarbons and a significant amount of benzene and heavier aromatics, and which is condensed and recycled to a lower portion of LLE column as reflux, and withdrawing a second solvent-rich stream containing solvent and polar hydrocarbons, which is substantially free of less polar hydrocarbons, from a bottom of the ESC;

(iv) introducing the second solvent-rich stream in step (iii) into a middle portion of the SRC, withdrawing a polar hydrocarbon-rich stream, which is substantially free of solvent and less polar hydrocarbons, from a top of the SRC, and removing a third solvent-rich stream from the bottom of the SRC;

(v) introducing a major portion of the third solvent-rich stream into the upper portion of the LLE column in step (i) as the selective solvent feed; and (vi) cooling a minor portion of the third solvent-rich stream in step (iv) and introducing the cooled minor portion of the third solvent-rich stream into an upper portion of a solvent cleanup zone to form the solvent phase; wherein step (c) comprises:

(vii) introducing the external stream into a lower portion of the solvent cleanup zone, as a heavy hydrocarbon displacement agent, to squeeze out heavy hydrocarbons and polymeric materials from the solvent phase into a hydrocarbon phase; and (viii) withdrawing an accumulated hydrocarbon phase containing heavy hydrocarbons and polymeric materials from an upper portion of the solvent clean-up zone and recovering the solvent phase containing solvent and polar hydrocarbons and having substantially reduced levels of heavy hydrocarbons and polymeric materials, from a lower portion of the solvent clean-up zone; and the method further comprises:

(ix) introducing the solvent phase from the solvent clean-up zone in step (viii) into a middle portion of the LLE column in step (i) as part of a hydrocarbon feed to recycle purified solvent into a solvent loop.

29. The method of claim wherein step (v) comprises:
introducing a major portion of the third solvent-rich stream into the upper portion of the LLE column in step (i) and introducing a first minor portion of the third solvent-rich stream into an upper portion of a high-temperature thermal solvent regeneration zone, recovering a fourth solvent-rich stream containing solvent, water, and hydrocarbons and other compounds having boiling points that are below that of the solvent, from a top of the solvent regeneration zone, and removing heavy sludge from a lower portion of the solvent regeneration zone; and wherein step (vi) comprises:
cooling a mixture comprising the fourth solvent-rich stream in step (v) and a second minor portion of the third solvent-rich stream in step (iv) and introducing the mixture into an upper portion of the solvent cleanup zone to form the solvent phase.

30. The method of claim 16 wherein the feed stream contains one or more petroleum products that is selected from reformate and pyrolysis gasoline.

* * * * *